(12) United States Patent
Zimmer

(10) Patent No.: US 8,702,630 B2
(45) Date of Patent: Apr. 22, 2014

(54) METHOD AND APPARATUS FOR INJECTING ULTRASOUND INTO TISSUE

(75) Inventor: Bernd Zimmer, Neu-Ulm (DE)

(73) Assignee: Zimmer Medizinsysteme GmbH, Neu-Ulm (DE)

( * ) Notice: Subject to any disclaimer, the term of this patent is extended or adjusted under 35 U.S.C. 154(b) by 1119 days.

(21) Appl. No.: 11/558,119

(22) Filed: Nov. 9, 2006

(65) Prior Publication Data

US 2007/0239076 A1    Oct. 11, 2007

(30) Foreign Application Priority Data

Nov. 11, 2005 (DE) .......................... 10 2005 053 918

(51) Int. Cl.
*A61H 1/00* (2006.01)

(52) U.S. Cl.
USPC .................................... 601/2; 600/437; 601/3

(58) Field of Classification Search
USPC ........................... 600/437, 439; 601/2; 604/22
See application file for complete search history.

(56) References Cited

U.S. PATENT DOCUMENTS

| | | | |
|---|---|---|---|
| 3,499,437 A | 3/1970 | Balamuth | |
| 4,530,360 A | 7/1985 | Duarte | |
| 5,209,221 A | 5/1993 | Riedlinger | |
| 5,413,550 A | 5/1995 | Castel | |
| 5,601,526 A * | 2/1997 | Chapelon et al. | 601/3 |
| 5,882,302 A * | 3/1999 | Driscoll et al. | 600/371 |
| 6,206,843 B1 * | 3/2001 | Iger et al. | 601/2 |
| 6,419,648 B1 | 7/2002 | Vitek et al. | |
| 6,451,013 B1 * | 9/2002 | Bays et al. | 606/27 |
| 6,500,141 B1 * | 12/2002 | Irion et al. | 604/22 |
| 6,514,220 B2 | 2/2003 | Melton, Jr. et al. | |
| 6,540,700 B1 | 4/2003 | Fujimoto et al. | |
| 6,565,520 B1 | 5/2003 | Young | |
| 6,589,174 B1 * | 7/2003 | Chopra et al. | 600/439 |
| 6,629,948 B2 | 10/2003 | Rockley et al. | |
| 6,645,162 B2 * | 11/2003 | Friedman et al. | 601/2 |
| 6,860,852 B2 * | 3/2005 | Schonenberger et al. | 600/439 |
| 2001/0003155 A1 | 6/2001 | Rockley et al. | |
| 2002/0049395 A1 * | 4/2002 | Thompson et al. | 601/2 |
| 2003/0018255 A1 * | 1/2003 | Martin et al. | 600/437 |

(Continued)

FOREIGN PATENT DOCUMENTS

| | | |
|---|---|---|
| DE | 3806532 | 9/1989 |
| DE | 10306795 | 9/2004 |
| JP | 2004-522503 | 7/2004 |
| WO | 98/07470 | 2/1998 |

OTHER PUBLICATIONS

English language Abstract of DE 10306795.

(Continued)

*Primary Examiner* — Tse Chen
*Assistant Examiner* — Mark Remaly
(74) *Attorney, Agent, or Firm* — Greenblum & Bernstein, P.L.C.

(57) ABSTRACT

In a method for driving an injection device for injecting ultrasound into a tissue, the ultrasound has a predetermined thermal effect and a predetermined mechanical effect in the tissue. Ultrasound pulses are successively injected utilizing the injection device. Each ultrasound pulse comprises a pulse width and a duty ratio of the ultrasound pulses is set as a function of the thermal and mechanical effects of the ultrasound pulses.

21 Claims, 4 Drawing Sheets

(56) References Cited

U.S. PATENT DOCUMENTS

| | | |
|---|---|---|
| 2003/0135084 A1 | 7/2003 | Young |
| 2003/0212351 A1* | 11/2003 | Hissong et al. .................. 601/2 |
| 2004/0082857 A1 | 4/2004 | Schonenberger et al. |
| 2004/0171970 A1* | 9/2004 | Schleuniger et al. ............ 601/2 |
| 2005/0085748 A1 | 4/2005 | Culp et al. |
| 2005/0261610 A1* | 11/2005 | Mast et al. ....................... 601/2 |

OTHER PUBLICATIONS

Japan Office action, dated Dec. 22, 2011 along with an english translation thereof.

Japan Office action, dated Nov. 26, 2012 along with an english translation thereof.

German Office Action for Application No. 10 2005 053 918.1, dated Feb. 7, 2014.

* cited by examiner

METHOD AND APPARATUS FOR INJECTING ULTRASOUND INTO TISSUE

BACKGROUND OF THE INVENTION

The present invention relates to a method and an apparatus for the injection of ultrasound into tissue parts to be treated, using ultrasound pulses.

In medical technology, ultrasound is used on the one hand as a diagnostic aid for imaging processes, and on the other hand is also used therapeutically. Ultrasound produces density waves in the tissue, which act as vibration and as heat. Ultrasound injection thus on the one hand achieves a mechanical effect which acts like micromassage in soft-tissue, and in the process, for example, stimulates the release of tissue hormones and influences the metabolism and muscle state. The stimulating effect of this mechanical component of therapeutic ultrasound can have a positive influence on tissue regeneration. The thermal component of the therapeutic ultrasound leads to tissue heating which is used, for example, during thermotherapy.

Therapeutic ultrasound is used both continuously and in pulse form. In the case of continuous injection, a suitable oscillation generator continuously produces ultrasound waves at a predetermined ultrasound frequency. In the case of pulsed ultrasound, pulses of ultrasound are produced. These pulses of ultrasound then have a pulse width or pulse length in the time domain, while the ultrasound is injected at the respective ultrasound frequency.

This is followed by a time interval with an injection pause, in which no injection whatsoever takes place. The number of such ultrasound pulses per unit time results in a pulse repetition frequency. The limit case of injection pauses turning to zero results in continuous ultrasound.

The therapeutic effect of the injected ultrasound in this case depends in particular on the selected ultrasound frequency, the duration of application, and also on the nature of the injected ultrasound pulses. By way of example, possible pulse parameters are the pulse width, the pulse length, the ultrasound frequency, the amplitude of the ultrasound and the pulse repetition frequency. The person carrying out the therapy has to in this case decide what power and in what signal form the therapeutic ultrasound must be used, and in some cases this is difficult to assess. Precise setting of the treatment depth in a tissue by ultrasound application is also frequently difficult.

Proposals have already been made in the past to inject ultrasound energy at different ultrasound frequencies from a plurality of ultrasound transmitters at the same time into a tissue that is to be treated. Published German application for patent No. 103 06 795 A1 discloses a corresponding ultrasound device in which a plurality of ultrasound beams at different frequencies act at a common focus area in the tissue at the same time. However, this results in the disadvantage of a high level of implementation complexity with a plurality of ultrasound sources and operation by the person carrying out the therapy, who must himself define a large number of parameters, such as the frequency, pulse lengths and injection power.

BRIEF DESCRIPTION OF THE INVENTION

One object of the present invention is thus to provide a method for the injection of ultrasound which can be matched particularly easily to the respective therapeutic requirements by the person carrying out the therapy.

The object is achieved in accordance with the invention by means of a method for driving an injection means for the injection of ultrasound into a tissue having a predetermined thermal effect and a predetermined mechanical effect in the tissue, with ultrasound pulses each having a pulse width being injected successively, and with the duty ratio of the ultrasound pulses being set as a function of the thermal and mechanical effect of the ultrasound.

The object is also achieved in accordance with the invention by means of method for driving an injection means for the injection of ultrasound into a tissue having a predetermined thermal effect at a predetermined tissue depth in the tissue, with ultrasound pulses being injected successively with a respective pulse width and at a respective ultrasound frequency, and with the pulse width ratio of the ultrasound pulses being set as a function of the predetermined tissue depth and the ultrasound frequencies.

The object is also achieved in accordance with the invention by means of an apparatus for the injection of ultrasound into a tissue, comprising:
  an input device for setting at least one mechanical, thermal effect and/or a treatment depth of the ultrasound in the tissue:
  a control device, which is designed in such a manner that the invnetive method is carried out, with the duty ratio for ultrasound pulses, pulse width ratios and/or frequency ratios being determined and with the control device producing appropriate control signals; and
  at least one ultrasound head, which is activated and deactivated as a function of the control signals and emits ultrasound pulses.

According to the invention, the respective person carrying out the therapy can preset both a thermal effect and a desired mechanical effect in the tissue to be treated, in accordance with his therapy requirements.

According to the invention, ultrasound pulses are then sequentially injected into the tissue, with, in particular, their duty ratio, that is to say the ratio of the period duration to the time period in which ultrasound power is being injected when ultrasound is emitted on a periodically pulsed basis, being determined automatically. Ultrasound heads having suitable oscillation generators are known as injection means. Sound heads with piezo-oscillation generators are frequently used.

In one embodiment of the inventive method, the following steps may be carried out:
  Predetermination of a mechanical effect parameter for the mechanical effect;
  Predetermination of a thermal effect parameter for the thermal effect;
  Definition of the duty ratio as a function of the thermal effect parameter and of the mechanical effect parameter; and
  Activation and deactivation of the injection means for the injection of ultrasound pulses with the defined duty ratio.

Pulse widths and sequences may be achieved according to the invention by switching the injection means on and off, or by activation and deactivation of the injection means.

In this case, the amplitude of the emitted ultrasound power is preferably used as the mechanical effect parameter. This is generally stated in $W/cm^2$ and depends essentially on the amplitude of the sound waves. The biological effect of this mechanical component of the ultrasound is based on reversible microcavitation and liquid movements in the tissue. The amplitude is thus an advantageous mechanical effect parameter which can be clearly understood by a person carrying out the therapy.

The ultrasound power which is effectively emitted into the tissue may be used as the thermal effect parameter. The power from the injected ultrasound, which is generally converted to friction, leads to increased Braunian movement and molecular friction, thus resulting in a temperature increase in the tissue. The respective heating depends not only on the amplitude of the ultrasound waves but also on the frequency and the total energy introduced, as well as on the application duration.

The maximum possible thermal effect may be determined from the predetermined mechanical effect or the corresponding effect parameter.

In one embodiment of the inventive method, the ultrasound pulses are at different ultrasound frequencies. The ultrasound pulses which are thus injected successively with a respective duty ratio that is governed according to the invention allow particularly precise determination of the penetration depth, and thus a form of therapy which can easily be adjusted in terms of the thermal, mechanical and local effect of the ultrasound.

An alternative embodiment of the method according to the invention for driving an injection means for the injection of ultrasound into a tissue having a predetermined thermal effect at a predetermined tissue depth in the tissue consists in that ultrasound pulses with a respective pulse width and at a respective ultrasound frequency are injected successively, with the pulse width ratio of the ultrasound pulses being set as a function of the predetermined tissue depth and of the ultrasound frequencies.

The following method steps may therefore be preferably carried out:
a) Predetermination of a tissue depth for a thermal effect of the ultrasound in the tissue,
b) Predetermination of at least one first and one second ultrasound frequency, with each ultrasound frequency being associated with a respective penetration depth in the tissue;
c) Definition of the pulse width ratio as a function of the thermal effect and of the associated penetration depths; and
d) Activation and deactivation of the injection means for the sequential injection of ultrasound pulses with the defined pulse width ratio.

In this case, each ultrasound frequency is preferably associated with a respective penetration depth in the tissue, and two different ultrasound frequencies are selected in such a manner that a predetermined treatment depth region is located between the two associated penetration depths in the tissue.

It is particularly preferable to select a frequency ratio of the different ultrasound frequencies in such a manner that a predetermined treatment depth is achieved in the tissue. The sequential injection of a plurality of ultrasound pulses at different frequencies according to the invention has the particular advantage that the required ultrasound power to achieve a plurality of treatment depths during therapy need not be increased in practice. This is the situation when only a single, fixed predetermined ultrasound frequency is injected in a pulsed form.

The thermal effect parameter and the mechanical effect parameter, the duty ratio, the frequency ratio and/or the treatment depth are/is preferably displayed on a display.

In one particularly preferred embodiment of the inventive method, respective duty ratios, pulse widths, frequency ratios, amplitudes and/or tissue types are stored in a databank. The method according to the invention thus allows particularly simple and specific treatment based on the therapeutic requirements, which essentially comprise the desired thermal and mechanical effect, and may depend on the respective body part to be treated.

In one aspect of the invention, an apparatus for the injection of ultrasound into a tissue, comprises an input device for setting at least one mechanical, one thermal effect and/or a treatment depth of the ultrasound in the tissue, a control device, which determines the duty ratio for ultrasound pulses, pulse width ratios and/or frequency ratios and produces appropriate control signals, and at least one ultrasound head, which is activated and deactivated as a function of the control signals and emits ultrasound pulses.

The control device in this case carries out the inventive method for the injection of ultrasound.

In this case, at least one display means is preferably provided for the selected mechanical effect and/or the thermal effect. A display means, for example in the form of a barchart, can thus reliably indicate to the person carrying out the therapy the selected or predetermined mechanical and thermal effect parameters which lead to the internally defined duty ratio and/or frequency ratio of the ultrasound pulses. This thus allows particularly simple and clear control of a corresponding ultrasound appliance.

The ultrasound head may be in the form of a multiple-frequency head.

A memory device may be provided and may be coupled to the control device, and may be used to store therapy forms and tissue types, duty ratios and ultrasound frequency details for selected mechanical effects. It is thus possible to program an appropriate parameter set relating to the duty ratios, frequencies and possibly further parameters for every combination of desired thermal and mechanical effect. In this case, on the one hand it is also possible to use empirical values obtained from experimental series, or alternatively the control device calculates the duty ratio using a predetermined determination algorithm. The thermal and mechanical effect is associated in a preferred manner with a duty ratio by the duty ratio being proportional to the ratio between the mechanical and the thermal effect parameters.

The invention also relates to a computer program product having a computer program which is stored in a machine-legible form in a memory means and causes the method according to the invention to be carried out on a computer, and in which the computer emits appropriate control signals for controlling the injection means, via an interface. A computer program product may, for example, be a floppy disk, a CD-ROM or some other memory medium which provides the method steps according to the invention for computer-implemented execution, in a coded form.

BRIEF DESCRIPTION OF THE DRAWINGS

Further advantageous refinements and developments of the invention are the subject matter of the dependent claims and of the exemplary embodiments which will be described in the following text with reference to the figures, in which:

Unless stated to the contrary, identical or functionally identical elements have been provided with the same reference symbols in the figures.

DETAILED DESCRIPTION OF THE INVENTION

Figure 1:
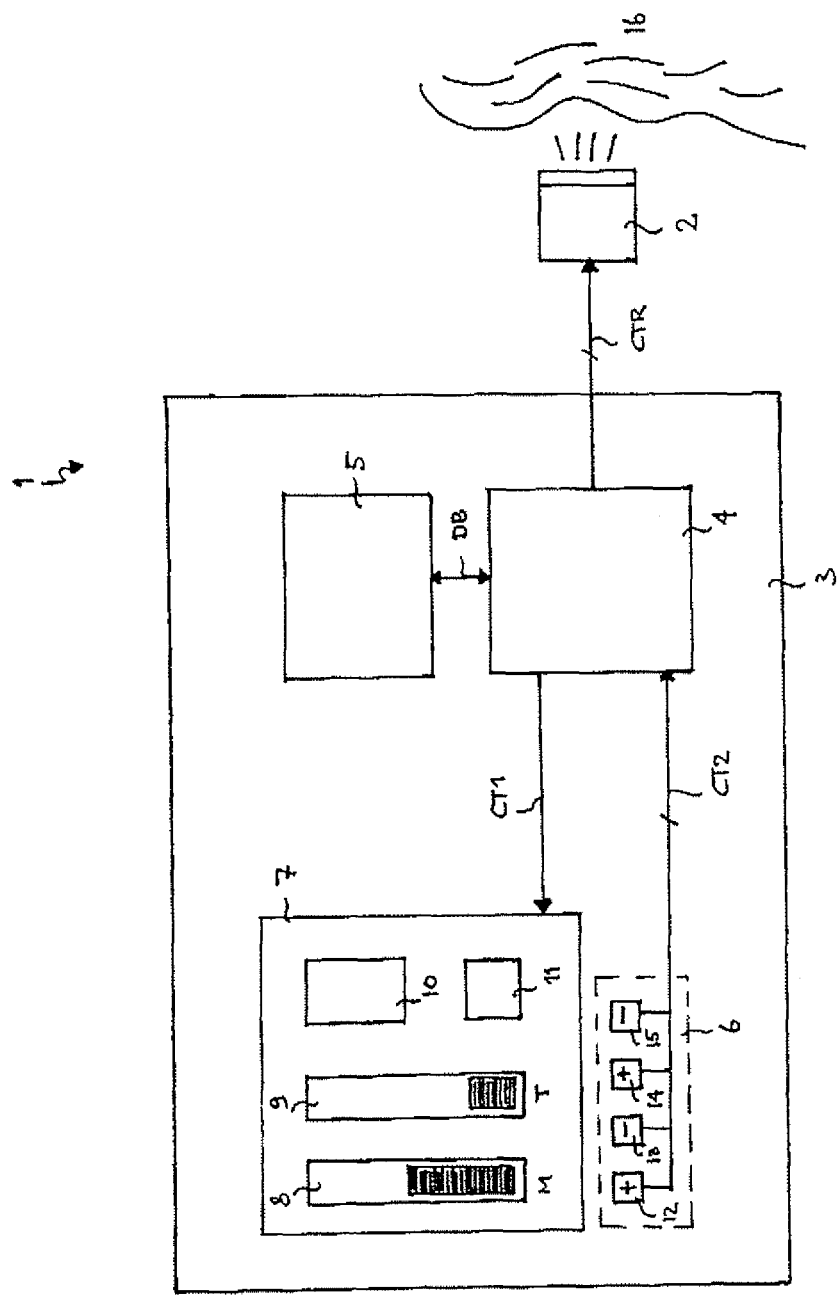
FIG. 1 is a block diagram of an apparatus for the injection of ultrasound.

FIG. 1 shows a block diagram of an apparatus according to the invention for the injection of ultrasound. In the exemplary embodiment illustrated here, the apparatus 1 has an ultrasound head 2 which is connected to a controller 3. The controller 3 may be in a computer-implemented form, for example, and supplies control signals CTR to the ultrasound head 2, which accordingly emits ultrasound into a tissue 16.

The controller has a control device 4 which is coupled to a memory 5 via a suitable bus DB. An input device 6 is also provided, by means of which a desired mechanical effect parameter and a desired thermal effect parameter for the respective ultrasound therapy can be entered, for example by someone carrying out the therapy. A display device 7 uses, for example, barcharts 8, 9 to display the selected effect parameters, and has further indications or displays 10, 11, by means of which, for example, it is possible to display the penetration depth, the coupling of the ultrasound waves to the tissue 16 or further details relating to the specific ultrasound therapy. The display device 7 and the input device 6 are coupled to the control device 4 via suitable control lines CT1, CT2. The two barcharts 8, 9 in this case indicate to the operator or to the person carrying out the therapy the selected thermal biological effect T on the tissue 16 that is subject to the therapy, in the form of the effective power $P_{eff}$ in suitable units, such as W/cm$^2$, as well as the selected mechanical biological effect M, on the tissue 16 to be irradiated, in the form of the amplitude of the power $P_{peak}$, likewise in W/cm$^2$. The required penetration depth can likewise be set, as well as the overall treatment duration.

Depending on the effect parameters $P_{peak}$ and $P_{eff}$, the control device 4 calculates or determines advantageous duty ratios for the pulsed emission of ultrasound waves at a frequency which is likewise predetermined. In this case, by way of example, association tables are stored in the memory 5 and associate combinations of ultrasound frequencies, of the effective power $P_{eff}$ and of the maximum amplitude of the power $P_{peak}$ with a respective duty ratio T1/T2.

Figure 2:
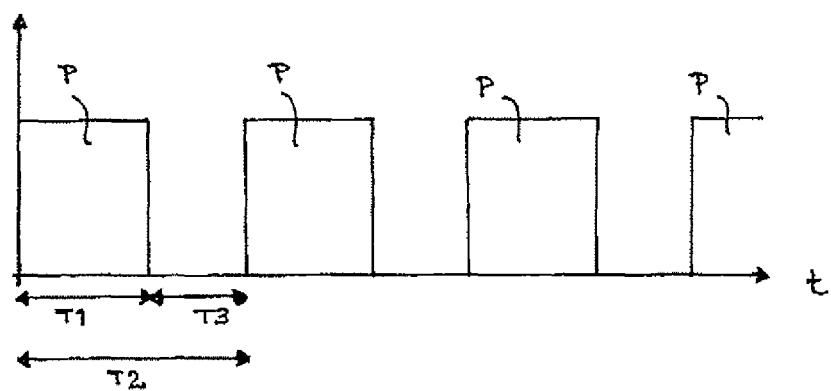
FIG. 2 are examples of signal waveforms of ultrasound pulses.

By way of example, FIG. 2 illustrates one possible time sequence of ultrasound pulses P. The ultrasound head 2 emits ultrasound pulses P with a period length T2, with one ultrasound pulse at the predetermined frequency, for example of 800 MHz, being emitted during a time T1. This is followed by a time period T3 with no ultrasound emission. The ratio T1/T2 indicates the duty ratio.

Figure 3A:
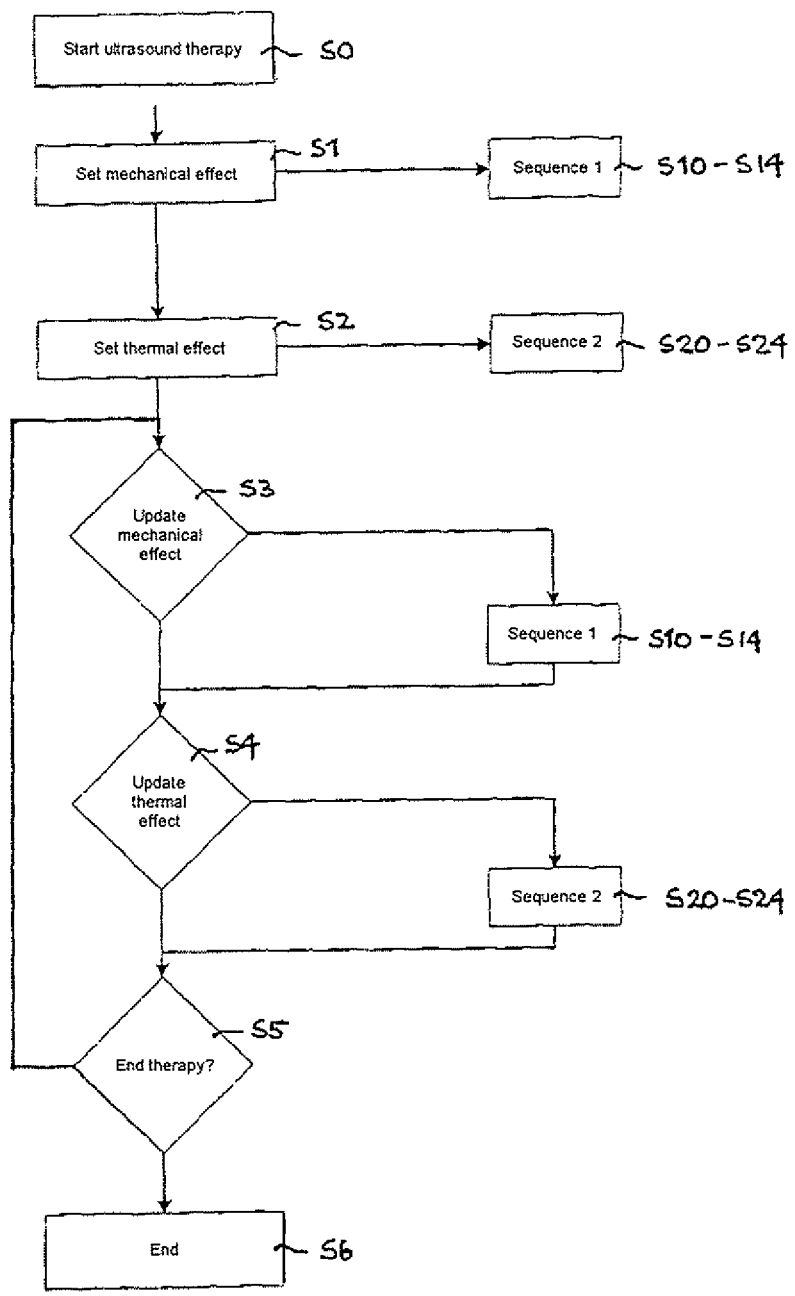
FIG. 3 is a flowchart illustrating the inventive method.
Figure 3C:
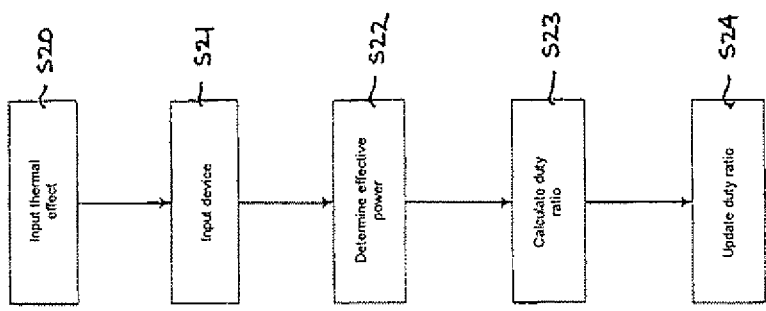
Figure 3B:
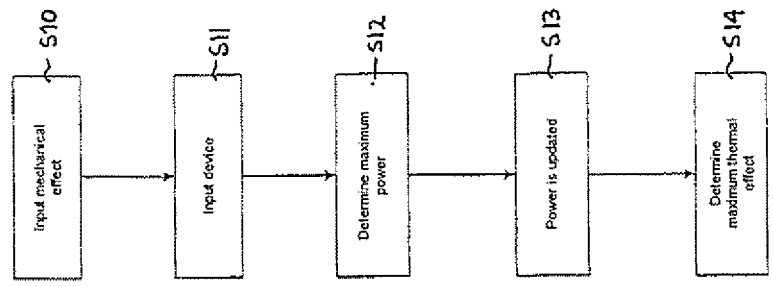

FIGS. 3A-3C show a flowchart of the method according to the invention. The method steps and calculation steps are essentially carried out by the control device 4 for the controller 3, which is illustrated in FIG. 3. The major steps for carrying out a therapeutic ultrasound application are shown in the sequence S0-S6.

The ultrasound therapy is started in step S0. The step S1 comprises the setting of the desired mechanical effect which is intended to be achieved by the ultrasound therapy. FIG. 3B shows the corresponding steps S10-S14. The person carrying out the therapy enters the mechanical effect M in step S10, via the keys 12, 13 on the input device 6 (step S11), and this is at the same time displayed qualitatively as a barchart 8 on the display 7. The person carrying out the therapy then enters the amplitude $P_{peak}$ of the power to be injected. The ultrasound power which results from this is determined from it in step S12, and is updated in step S13. The maximum possible thermal effect is determined in step S14, and is obtained from the effective power $P_{eff}$, which in turn depends on the selected amplitude $P_{peak}$.

The desired thermal effect T is selected in the next step S2 on the basis of the power, selected by the person carrying out the therapy, to be emitted into the tissue. The desired thermal effect T is entered in step S20 as a thermal effect parameter in the form of $P_{eff}$. This is transmitted to the control device 4 from the input device 6 in step S21. The appropriate effective power is determined from the selected desired power or dose (step S22).

In the next step S23, the control device 4 determines an appropriate duty ratio T1/T2 for pulsed ultrasound injection. In this case, the ratio $P_{peak}/P_{eff}$ corresponds to the duty ratio T1/T2. The corresponding association of the thermal and mechanical effect T, M with the duty ratio T1/T2 taking account of the respective ultrasound frequency is stored in the memory 5. Finally, the combination of ultrasound frequency and duty ratio T1/T2 determined in this way is updated in step S24, and is transmitted via control signals CTR to the ultrasound head 2.

This now results in pulsed injection of ultrasound which corresponds exactly to the therapeutic requirements of the operator, without the operator or the person carrying out the therapy having to give particular consideration as to how the pulse sequence must be set with respect to the duty ratio T1/T2.

If the mechanical effect M is varied during the therapy in a step S3 by variation of the selected effect parameter, this also results in the desired thermal effect T being varied or updated by variation of the effect parameter, once again resulting in a sequence as is illustrated in FIG. 3C.

Once the tissue subject to the therapy has been irradiated appropriately, the therapy is ended (step S5) and the ultrasound injection ceases (step S6).

The steps illustrated in FIG. 3A, in particular the updates to the respective mechanical and thermal effect (steps S3, S4) can also be carried out in a programmed form, so that the control device 4 reads an appropriate therapy sequence from the memory 5, and injects ultrasound via the ultrasound head 2. To this extent, a check can be carried out in step S5 to determine whether all of the therapy steps have already been carried out, or whether the steps S3-S4 should be carried out once again.

In addition to the automatic determination and selection of the duty ratio T1/T2 from the appropriate effect parameters for the purpose of carrying out the therapy, in terms of the mechanical and thermal effect M, T in the tissue, the invention provides for a particularly good depth effect to be achieved, and for a predetermined range of treatment depths to be irradiated specifically by the emission of ultrasound pulses at different frequencies.

The penetration depth Z of the ultrasound depends essentially on the selected ultrasound frequency f, and generally falls as the frequency rises. The expression the 3 dB depth is referred to, at which the intensity I(z) of the ultrasound radiation in the tissue has fallen by 50%. At 800 KHz, the ultrasound intensity in muscle tissue falls to 50% after about 2.9 cm. This 3 dB depth is, however, only 0.77 cm at 3 MHz. The decrease in intensity as a function of the tissue depth is generally based on an exponential relationship:

$$I(z) = I_0 e^{-\alpha \cdot f \cdot z}, \quad \text{(Equation 1)}$$

$I_0$ being the effective value at the depth z=0, α being a decay parameter which is tissue-dependent, and f being the ultrasound frequency.

For heat generation at a tissue depth z as a result of injected ultrasound waves, it can be shown that there is an optimum ultrasound frequency for every tissue depth that it is desired to heat. The heat generated depends on the decrease in the power density as a function of the tissue depth and the ultrasound frequency. In this case it is possible to convert more power to heat at high frequencies than at low frequencies, up to a specific depth, for example 2 cm in the case of skeletal musculature. However, beyond the tissue depth of 2 cm, lower frequencies produce more heat than higher frequencies. The tissue depth at which the greatest amount of heat is generated can thus be selected by adjustment of the ultrasound frequency.

In general, lower frequencies between 0.5 and 1.5 MHz have their optimum effect in terms of heat generation at a relatively great depth. At frequencies from 3 MHz, the optimum depth is in the order of magnitude of 1 cm, and is still only slightly dependent on the frequency. Investigations by the applicant have shown that an advantageous frequency range of between 0.7 and 2.5 MHz is a good setting for the heat generated by ultrasound.

Ultrasound oscillators and ultrasound heads for the emission of ultrasound waves are normally designed for a single ultrasound frequency. In general, however, it is also possible to emit integer multiples of this fundamental frequency from the ultrasound head. Typical frequencies are multiples of 800 KHz, that is to say 1.6 and 2.4 MHz. The optimum depths for heat generation are in this case 4.17 cm at 0.8 MHz and 1.39 cm at 2.4 MHz. In order to efficiently treat a tissue layer located between these depths with heat by the application of ultrasound, it would, however, have to be possible to produce an intermediate value between 0.8 and 2.4 MHz. This is generally not possible.

The invention now provides, in order to simulate the optimum depth for heat development by ultrasound, for ultrasound pulses to be injected alternately at the fundamental frequency of 0.8 MHz, and three times this frequency, that is to say 2.4 MHz. This results in an optimum depth for conversion to heat at a depth between the limit depths of 1.39 cm and 4.17 cm, provided that the switching between the injected frequencies takes place more quickly than the thermal time constant in the tissue. The thermal time constant predetermines the time in which the temperature of a heat store, for example a tissue area in this case, is still only about 63% of the initial temperature as a result of heat losses.

In order, for example, to simulate an optimum depth for heat generation of 2.78 cm, an ultrasound pulse is injected for a time of one second at 0.8 MHz, for example, followed alternately, according to the invention, by a pulse at 2.4 MHz for one second. This results in the optimum depth being 2.78 cm=(4.17 cm+1.39 cm)/2. In this simple case, the duty ratio is T1/T2=1 for each ultrasound pulse. In principle, a desired treatment depth can be selected using the following equation:

$$Z(TG) = \frac{1}{TG}[Z(TP1) \cdot TP1 + Z(TP2) \cdot TP2] \quad \text{(Equation 2)}$$

In this case, Z(TG) is the desired treatment depth, TG=TP1+TP2 is the duration of an ultrasound cycle according to the invention, TP1 and TP2 are the pulse lengths of the two ultrasound pulses P1, P2 at a respective frequency f1, f2. Z(TP1) is the optimum effective depth, that is to say the tissue depth at which the maximum power density is converted to heat, for the ultrasound pulse P1, and analogously Z(TP2) for TP2.

Figure 4:
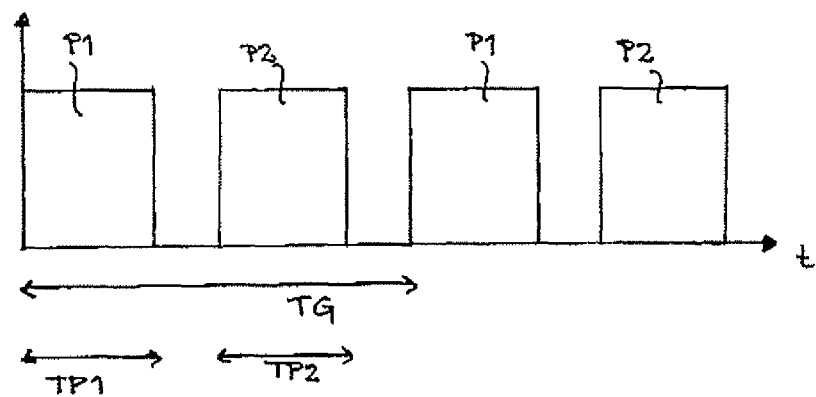
FIG. 4 is a schematic illustration of ultrasound pulses produced according to the invention.

FIG. 4 illustrates corresponding ultrasound pulse sequences produced according to the invention. Ultrasound pulses P1 and P2 with a respective pulse duration of TP1 and a respective frequency of f1 and f2 are provided alternately, in order to achieve a treatment depth based on Equation 2. FIG. 4 furthermore shows a respective duty ratio for the ultrasound pulses P1, P2 which is not equal to 1.

Thus, according to the invention, not only is it possible to set the treatment depth precisely but also the desired thermal and mechanical effect for the therapy. In order to carry out a therapy at a treatment depth which is predetermined by the user and generally by the use of frequencies which are predetermined by the ultrasound head, the operator just has to enter the effect parameters and treatment depth on the controller. Corresponding ultrasound pulse lengths, frequencies and duty ratios are then determined automatically by the controller 3 according to the invention.

In particular, the present invention makes it possible to implement the requirements defined by the person carrying out the therapy for the ultrasound therapy in a particularly simple manner. The automatic determination of the duty ratio of the ultrasound pulses to be injected, as well as the pulse duration and frequency, in order to define the desired treatment depth, is carried out automatically. The method according to the invention for sequential injection of ultrasound pulses at different frequencies makes it possible to define continuously variable treatment depths, even when only a limited number of different ultrasound frequencies are provided. It is thus also possible to reduce the number of ultrasound heads required in a therapy practice.

Although the present invention has been explained in more detail with reference to preferred exemplary embodiments, it is not restricted to these but can be modified in many ways. The described signal waveforms should be regarded only as examples. Different ultrasound frequencies may be used, of course, and different known display means may be used for the effect parameters. Variables derived from $P_{peak}$ and $P_{eff}$ may also be used as effect parameters, for example the respective emitted power, which is quoted in J/cm². In particular, the controller according to the invention can also directly generate ultrasound signals which have signal waveforms according to the invention. To this extent, the control signals can also themselves be understood as ultrasound signals. A computer-implemented embodiment of the invention as a computer program is, of course, also possible.

What is claimed is:

1. A method for driving an injection device for injecting ultrasound into a tissue, the ultrasound having a predetermined thermal effect and a predetermined mechanical effect in the tissue, the method comprising:
    predetermining a mechanical effect parameter for the mechanical effect;
    predetermining a thermal effect parameter for the thermal effect;
    defining a duty ratio as a function of the thermal effect parameter and of the mechanical effect parameter;
    injecting a sequence of ultrasound pulses, the sequence comprising first ultrasound pulses and second ultrasound pulses respectively having different ultrasound frequencies, the sequence having a single first ultrasound pulse following a single second ultrasound pulse and the single second ultrasound pulse following the single first ultrasound pulse;
    wherein one of the ultrasound frequencies is an integer multiple of the other ultrasound frequency utilizing the injection device, each of the ultrasound pulses comprising a pulse width,
    wherein the duty ratio of the ultrasound pulses at the predetermined ultrasound frequency is set as a function of the thermal and mechanical effect parameters of the ultrasound, and the duty ratio is defined as a ratio of a first time period of emission of one ultrasound pulse at the predetermined frequency divided by a second time period, the second time period being a sum of the first time period and a time period following the first time period and having no ultrasound emission, and activating and deactivating the injection device for injecting the ultrasound pulses having the duty ratio,
wherein an amplitude of an emitted ultrasound power of the ultrasound pulses is utilized as the mechanical effect parameter or an emitted power of the ultrasound pulses is utilized as the thermal effect parameter.

2. The method of claim 1, wherein the defining sets the duty ratio to unity.

3. The method of claim 1, further comprising displaying at least one of the thermal effect parameter, the mechanical effect parameter, and the duty ratio.

4. The method of claim 1, further comprising storing at least one of duty ratios, and the pulse widths for at least one of predetermined therapy forms and tissue types in a databank.

5. The method according to claim 1, wherein the defining defines the duty ratio by dividing the amplitude of the emitted power of the ultrasound pulses by the effectively emitted power of the ultrasound pulses.

6. A method for driving an injection device for injecting ultrasound into a tissue, the ultrasound having a predetermined thermal effect at predetermined tissue depth in the tissue, the method comprising injecting a sequence of successive ultrasound pulses, the sequence including first ultrasound pulses and second ultrasound pulses respectively having pulse widths and different ultrasound frequencies, the sequence having a single first ultrasound pulse following a single second ultrasound pulse and the single second ultrasound pulse following the single first ultrasound pulse, wherein a ratio of the pulse length of the first ultrasound pulse to the pulse length of the second ultrasound pulse is set as a function of the predetermined tissue depth which depends on the ultrasound frequencies of the first and second ultrasound pulses, wherein the first and second ultrasound pulses having different ultrasound pulses are alternately injected, and one of the ultrasound frequencies is an integer multiple of the other ultrasound frequency.

7. The method of claim 6, further comprising:
predetermining the tissue depth for the thermal effect;
predetermining at least one first ultrasound frequency and one second ultrasound frequency, each of the ultrasound frequencies being associated with a respective penetration depth in the tissue;
defining the pulse width ratio as a function of the thermal effect and of the penetration depths; and
activating and deactivating the injection device with the pulse width ratio.

8. The method of claim 6, wherein each of the ultrasound frequencies is associated with a respective penetration depth in the tissue, and wherein two different ultrasound frequencies are selected in such a manner that a predetermined treatment depth region in the tissue is located between two penetration depths associated with the selected two ultrasound frequencies in the tissue.

9. The method of claim 6, further comprising selecting the ultrasound frequencies such that the predetermined treatment depth in the tissue is achieved.

10. The method of claim 6, further comprising setting a duty ratio to unity.

11. The method of claim 7, further comprising displaying at least one of the thermal effect parameter, a mechanical effect parameter, a duty ratio, a frequency ratio, and the treatment depth on a display.

12. The method of claim 6, further comprising storing at least one of the duty ratios, pulse widths, and frequency ratios for at least one of a predetermined therapy forms or tissue types in a databank.

13. An apparatus for injecting ultrasound into a tissue, comprising:
an input that sets at least one of a mechanical effect, a thermal effect, or a treatment depth of ultrasound injected by said apparatus in a tissue;
a controller configured to perform the method according to claim 6, wherein at least one of duty ratios for the ultrasound pulses, the pulse width ratio, and frequency ratios is determined and wherein said controller produces appropriate control signals; and
at least one ultrasound head that is activated and deactivated as a function of the control signals and that emits the ultrasound pulses.

14. The apparatus of claim 13, further comprising at least one display for displaying at least one of the mechanical effect, the thermal effect and the treatment depth set by the input.

15. The apparatus of claim 13, wherein said at least one ultrasound head comprises a multiple-frequency head.

16. The apparatus of claim 13, further comprising a memory device which is coupled to said controller and presets duty ratios and ultrasound frequency details for selected mechanical and thermal effects, therapy forms and tissue types.

17. The apparatus of claim 13, wherein said controller is configured to determine the duty ratio by executing a predetermined determination algorithm.

18. The apparatus for injecting ultrasound into a tissue according to claim 13, wherein the input is at least one key.

19. A non-transitory, tangible computer program product comprising a computer-readable medium storing a computer program that causes a computer to emit control signals to the injection device via an interface, the control signals causing the injection device to perform the method according to claim 1.

20. An apparatus for injecting ultrasound into a tissue, comprising:
an input that sets at least one of a mechanical effect, a thermal effect, and a treatment depth of ultrasound injected by said apparatus in a tissue;
a controller configured to perform the method according to claim 1, wherein the duty ratio for the ultrasound pulses is determined and wherein said controller produces appropriate control signals; and
at least one ultrasound head that is activated and deactivated as a function of the control signals and that emits the ultrasound pulses.

21. A non-transitory, tangible computer program product comprising a computer-readable medium storing a computer program that causes a computer to emit control signals to the injection device via an interface, the control signals causing the injection device to perform the method according to claim 6.

* * * * *